United States Patent [19]

Pressman et al.

[11] Patent Number: 5,760,272
[45] Date of Patent: Jun. 2, 1998

US005760272A

[54] METHOD FOR PREPARING DIARYL CARBONATES WITH IMPROVED SELECTIVITY

[75] Inventors: Eric James Pressman, East Greenbush; Sheldon Jay Shafer, Clifton Park, both of N.Y.

[73] Assignee: General Electric Company, Schenectady, N.Y.

[21] Appl. No.: 823,785

[22] Filed: Mar. 24, 1997

[51] Int. Cl.[6] .................... C07C 68/00; C07C 69/96
[52] U.S. Cl. ................. 558/274; 558/270; 558/271; 558/272; 558/273
[58] Field of Search ...................... 558/274, 270, 558/271, 272, 273

[56] References Cited

U.S. PATENT DOCUMENTS

| 4,187,242 | 2/1980 | Chalk | 558/274 |
|---|---|---|---|
| 5,231,210 | 7/1993 | Joyce et al. | 558/274 |
| 5,284,964 | 2/1994 | Pressman et al. | 558/274 X |
| 5,502,232 | 3/1996 | Buysch et al. | 558/270 |

*Primary Examiner*—Michael G. Ambrose
*Attorney, Agent, or Firm*—William H. Pittman; Douglas E. Stoner

[57] ABSTRACT

Hydroxyaromatic compounds such as phenol are converted to diaryl carbonates by reaction with oxygen and carbon monoxide in the presence of a catalyst package and an added diluent free from active hydrogen. The preferred catalyst packages comprise a Group VIIIB metal or salt thereof, an inorganic cocatalyst, and organic cocatalysts and a bromide or chloride source. The amount of added diluent is an effective amount to improve selectivity to diaryl carbonate. Preferred diluents are diphenyl carbonate and N-methylpyrrolidone.

19 Claims, No Drawings

METHOD FOR PREPARING DIARYL CARBONATES WITH IMPROVED SELECTIVITY

BACKGROUND OF THE INVENTION

This invention relates to the preparation of diaryl carbonates by carbonylation. More particularly, it relates to the improvement of selectivity to diaryl carbonate in the carbonylation reaction.

Diaryl carbonates are valuable intermediates for the preparation of polycarbonates by transesterification with bisphenols in the melt. This method of polycarbonate preparation has environmental advantages over methods which employ phosgene, a toxic gas, as a reagent and environmentally detrimental chlorinated aliphatic hydrocarbons such as methylene chloride as solvents.

Various methods for the preparation of diaryl carbonates by a carbonylation reaction of hydroxyaromatic compounds with carbon monoxide and oxygen have been disclosed. In general, the carbonylation reaction requires a rather complex catalyst. Reference is made, for example, to U.S. Pat. No. 4,187,242, in which the catalyst is Group VIIIB metal, i.e., a metal selected from the group consisting of ruthenium, rhodium, palladium, osmium, iridium and platinum, or a complex thereof.

Further developments in the carbonylation reaction, including the use of such cocatalysts as cobalt pentadentate complexes and terpyridines, are disclosed in U.S. Pat. Nos. 5,231,210, 5,284,964 and 5,399,734. These patents also disclose the use of quaternary ammonium or phosphonium halides, as illustrated by tetra-n-butylammonium bromide, as part of the catalyst package. The use of hexaalkylguanidinium salts in place of quaternary salts is disclosed in copending provisional application Ser. No. [RD-25209].

Formation of diaryl carbonates in the carbonylation reaction is accompanied by formation of by-products such as biphenols in varying proportions. The "selectivity" parameter is employed to measure the proportion of desired product, selectivity to diaryl carbonate being the amount of diaryl carbonate produced as a percentage of total reaction products. It would be desirable to suppress the formation of such by-products, maximizing selectivity to diaryl carbonate in the carbonylation reaction.

SUMMARY OF THE INVENTION

It has been discovered that by incorporation of diluents in the carbonylation reaction mixture in various proportions, typically below about 50% by weight of total reaction mixture, selectivity to diaryl carbonate can be significantly improved.

Accordingly, the invention is a method for preparing a diaryl carbonate which comprises contacting at least one hydroxyaromatic compound with oxygen and carbon monoxide in the presence of an amount effective for carbonylation of at least one catalytic material, and an added amount effective to improve selectivity of at least one organic diluent free from active hydrogen.

DETAILED DESCRIPTION; PREFERRED EMBODIMENTS

Any hydroxyaromatic compound may be employed in the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl)propane or "bisphenol A", whereupon the products are polycarbonates.

Other essential reagents in the method of this invention are oxygen and carbon monoxide, which react with the phenol to form the desired diaryl carbonate.

Any catalytic material effective in the carbonylation reaction may be employed. One generally preferred catalyst constituent is one of the Group VIIIB metals, preferably palladium, or a compound thereof. Thus, palladium black or elemental palladium deposited on carbon are suitable, as well as palladium compounds such as halides, nitrates, carboxylates, salts with aliphatic β-diketones and complexes involving such compounds as carbon monoxide, amines, phosphines and olefins. Preferred in most instances are palladium(II) salts of organic acids, most often $C_{2-6}$ aliphatic carboxylic acids, and of β-diketones such as 2,4-pentanedione. Palladium(II) acetate and the palladium(II) salt of 2,4-pentanedione are generally most preferred; the use of the 2,4-pentanedione salt as a catalyst constituent is disclosed and claimed in copending, commonly owned application Ser. No. 08/823,784.

The catalytic material preferably also includes an inorganic cocatalyst of the type disclosed in the aforementioned U.S. Pat. No. 5,231,210 and/or an organic cocatalyst of the type disclosed in the aforementioned U.S. Pat. No. 5,284,964. It is preferred to employ both an inorganic and an organic cocatalyst.

Typical inorganic cocatalysts are complexes of cobalt(II) salts with organic compounds capable of forming complexes, especially pentadentate complexes, therewith. Illustrative organic compounds of this type are nitrogen-heterocyclic compounds including pyridines, bipyridines, terpyridines, quinolines, isoquinolines and biquinolines; aliphatic polyamines such as ethylenediamine and tetraalkylethylenediamines; crown ethers; aromatic or aliphatic amine ethers such as cryptanes; and Schiff bases. The especially preferred inorganic cocatalyst is a cobalt(II) complex with bis[3-(salicylalamino)propyl]methylamine, said complex hereinafter being designated "CoSMDPT".

Suitable organic cocatalysts include various terpyridine, phenanthroline, quinoline and isoquinoline compounds including 2,2':6',2"-terpyridine, 4'-methylthio-2,2':6',2"-terpyridine and 2,2':6',2"-terpyridine N-oxide, 1,10-phenanthroline, 2,4,7,8-tetramethyl-1,10-phenanthroline, 4,7-diphenyl-1,10-phenanthroline and 3,4,7,8-tetramethyl-1,10-phenanthroline. The terpyridines and especially 2,2':6', 2"-terpyridine are generally preferred.

The catalytic material also contains a chloride or bromide, preferably bromide, source . It may be a quaternary ammonium or phosphonium salt, as disclosed in the aforementioned patents, or a hexaalkylguanidinium chloride or bromide as disclosed in copending provisional application Ser. No. [RD-25209]. The guanidinium salts are often preferred; they include the α, ω-bis(pentaalkylguanidinium)alkane salts. Salts in which the alkyl groups contain 2–6 carbon atoms and especially hexaethylguanidinium bromide are particularly preferred.

According to the present invention, there is added to the reaction mixture an amount effective to improve selectivity of at least one organic diluent. By "diluent" is meant a material that dilutes the reaction mixture, whether or not it serves as a solvent for the reactants or catalyst components. The suitable organic diluents are those which are free from active hydrogen atoms such as those present in hydroxy and amino groups.

Organic diluents which may be employed include aliphatic hydrocarbons such as hexane and octane, aromatic hydrocarbons such as toluene and xylene, alkoxyaromatic compounds such as anisole, dipolar aprotic solvents such as dimethylformamide and N-methylpyrrolidone, and diaryl carbonates such as diphenyl carbonate. In general, the aromatic hydrocarbons are not preferred since they tend to decrease the carbonylation rate, and dimethylformamide is not preferred unless highly purified since it may contain primary amines, having active hydrogen atoms, as impurities. The preferred compounds, apart from the above reservation concerning dimethylformamide, are the dipolar aprotic solvents and diaryl carbonates, with N-methylpyrrolidone and diphenyl carbonate being most preferred.

The proportion of organic diluent employed is an effective proportion to improve selectivity. This proportion will vary with the diluent employed, and optimum ranges therefor can be determined by simple experimentation. For the most part, the diluent proportion is in the range of about 1–40% by weight of total reaction mixture; i.e., total of reactants, catalyst constituents and diluent. In particular, the preferred level of added diphenyl carbonate is generally about 10–40%, preferably about 10–20%, and that for N-methylpyrrolidone is about 1–25%.

The proportion of Group VIIIB metal source employed is an amount sufficient to provide about 1 gram-atom of metal per 800–10,000 and preferably 2,000–5,000 moles of hydroxyaromatic compound. For each gram-atom of Group VIIIB metal there is usually employed about 0.1–5.0 and especially about 0.5–1.5 gram-atoms of cobalt, about 0.1–3.0 and preferably about 0.3–1.0 moles of organic cocatalyst and about 5–150, preferably about 20–50, moles of chloride or bromide source.

Gas is supplied to the reaction mixture in proportions of about 2–50 mole percent oxygen, with the balance being carbon monoxide. The gases may be introduced separately or as a mixture, to a total pressure in the range of about 10–250 atmospheres. Reaction temperatures in the range of about 60°–150° C. are typical. Drying agents, typically molecular sieves, may be present in the reaction vessel. In order for the reaction to be as rapid as possible, it is preferred to maintain the reaction pressure in accordance with the aforementioned U.S. Pat No. 5,399,734 until conversion of the hydroxyaromatic compound is complete.

The diaryl carbonates produced by the method of this invention may be isolated by conventional techniques. It is often preferred to form and thermally crack an adduct of the diaryl carbonate with the hydroxyaromatic compound, as described in U.S. Pat. Nos. 5,239,106 and 5,312,955.

The invention is illustrated by the following examples. Proportions of reagents, though described as constant for all examples, varied in certain instances by reason of batch size approximation; however, experience has shown that such differences in proportions are not material with respect to product yield, conversion and the like.

EXAMPLE 1

A constant composition gas flow reactor system, as disclosed in the aforementioned U.S. Pat. No. 5,399,734, was charged with 550 mmol of phenol, 3.25 mmol of hexaethylguanidinium bromide, 0.307 mmol of CoSMDPT, 0.100 mmol of 2.2':6',2"-terpyridine, 0.287 mmol of palladium(II) acetate and various quantities of diphenyl carbonate. Molecular sieves, 37 g, were placed in a perforated polytetrafluoroethylene basket mounted to the stir shaft of the reactor.

The reactor was sealed and heated to 110° C., with stirring, and a mixture of 12.9 mole percent oxygen and 87.1 mole percent carbon monoxide was introduced at a flow rate of 344 ml/min and a pressure of about 41 atmospheres. Gas flow was continued for 2 hours, after which a portion of the reaction mixture was removed and analyzed by high pressure liquid chromatography.

The results are given in Table I, in comparison with a control in which no diphenyl carbonate was added to the reaction mixture. The proportion of added diphenyl carbonate in Table I is based on total reaction mixture, including said added diphenyl carbonate. Diphenyl carbonate yields are of newly formed material, excluding originally added material.

TABLE 1

| Added diphenyl carbonate, % | Diphenyl carbonate yield, % | Diphenyl carbonate selectivity, % |
|---|---|---|
| 0 | 40.4 | 93 |
| 16.3 | 36.1 | 100 |
| 32.9 | 25.5 | 100 |
| 50.1 | 17.0 | 85.5 |

It is apparent that selectivity to diphenyl carbonate is substantially improved with the introduction of added diphenyl carbonate in proportions below 40%. Moreover, while some decrease in yield is noted at higher added diphenyl carbonate levels, only minor decreases are observed at added diphenyl carbonate levels up to 20%. Levels above 50%, however, resulted in substantial decreases in both yield and selectivity.

EXAMPLE 2

The reactor employed in Example 1 was charged with 630 mmol of phenol, 3.27 mmol of hexaethylguanidinium bromide, 0.304 mmol of CoSMDPT, 0.096 mmol of 2.2':6', 2"-terpyridine, 0.287 mmol of palladium(II) 2,4-pentanedionate and various quantities of N-methylpyrrolidone. The carbonylation reactions were conducted under conditions identical to those in Example 1. The results are given in Table II.

TABLE II

| N-Methylpyrrolidone, % | Diphenyl carbonate yield, % | Diphenyl carbonate selectivity, % |
|---|---|---|
| 0 | 45.6 | 81.9 |
| 3 | 49.5 | 91.2 |
| 8 | 50.4 | 92.7 |
| 16 | 51.0 | 99.9 |

It is apparent that selectivity is substantially improved by the addition of N-methylpyrrolidone. Moreover, said improvement in selectivity is not achieved at the expense of diphenyl carbonate yield.

What is claimed is:

1. A method for preparing a diaryl carbonate which comprises contacting at least one hydroxyaromatic compound with oxygen and carbon monoxide in the presence of an amount effective for carbonylation of at least one catalytic material, and an added amount effective to improve selectivity of at least one organic diluent selected from the group consisting of N-methylpyrrolidone and diaryl carbonates.

2. A method according to claim 1 wherein the catalytic material comprises a Group VIIIB metal or a compound thereof an inorganic cocatalyst, an organic cocatalyst and a bromide or chloride source.

3. A method according to claim 2 wherein the catalytic material comprises palladium(II) acetate or palladium(II) 2,4-pentanedionate.

4. A method according to claim 3 wherein the hydroxyaromatic compound is phenol.

5. A method according to claim 2 wherein the inorganic cocatalyst is a cobalt(II) salt with an organic compound capable of forming a pentadentate complex.

6. A method according to claim 5 wherein the organic compound is bis[3-(salicylalamino)propyl]methylamine.

7. A method according to claim 6 wherein the hydroxyaromatic compound is phenol.

8. A method according to claim 2 wherein the organic cocatalyst is a terpyridine, phenanthroline, quinoline or isoquinoline compound.

9. A method according to claim 8 wherein the organic cocatalyst is 2,2':6',2"-terpyridine.

10. A method according to claim 9 wherein the hydroxyaromatic compound is phenol.

11. A method according to claim 2 wherein the chloride or bromide source is a quaternary ammonium bromide, quaternary phosphonium bromide or hexaalkylguanidinium bromide.

12. A method according to claim 11 wherein the bromide source is a $C_{2-6}$ hexaalkylguanidinium bromide.

13. A method according to claim 12 wherein the hexaalkylguanidinium bromide is hexaethylguanidinium bromide.

14. A method according to claim 13 wherein the hydroxyaromatic compound is phenol.

15. A method according to claim 2 wherein the diluent is diphenyl carbonate.

16. A method according to claim 15 wherein the proportion of added diphenyl carbonate is about 10–40% by weight of total reaction mixture.

17. A method according to claim 2 wherein the diluent is N-methylpyrrolidone.

18. A method according to claim 17 wherein the proportion of N-methylpyrrolidone is about 1–25% by weight of total reaction mixture.

19. A method according to claim 2 wherein the inorganic cocatalyst is a complex of a cobalt(II) salt with an organic compound capable of forming a complex therewith, the bromide or chloride source is a hexaalkylguanidinium bromide, the proportions of oxygen and carbon monoxide are about 2–50 mole percent oxygen with the balance being carbon monoxide; the proportion of Group VIIIB metal is about 1 gram-atom per 2,000–5,000 moles of hydroxyaromatic compound; and about 0.5–1.5 gram-atoms of cobalt, about 0.3–1.0 mole of organic cocatalyst and about 20–50 moles of hexaalkylguanidinium bromide are employed per gram-atom of Group VIIIB metal.

* * * * *